US008684937B2

(12) United States Patent
Sasady

(10) Patent No.: US 8,684,937 B2
(45) Date of Patent: Apr. 1, 2014

(54) IMAGING PROBE

(75) Inventor: Niels-Christian Sasady, Frederiksberg (DK)

(73) Assignee: B-K Medical APS, Herlev (DK)

( * ) Notice: Subject to any disclaimer, the term of this patent is extended or adjusted under 35 U.S.C. 154(b) by 203 days.

(21) Appl. No.: 13/050,452

(22) Filed: Mar. 17, 2011

(65) Prior Publication Data

US 2012/0238879 A1    Sep. 20, 2012

(51) Int. Cl.
*A61B 8/12*    (2006.01)

(52) U.S. Cl.
USPC .............................. 600/462; 600/459; 901/31

(58) Field of Classification Search
USPC .................... 600/462, 459; 901/31
See application file for complete search history.

(56) References Cited

U.S. PATENT DOCUMENTS

| | | | | |
|---|---|---|---|---|
| 5,752,517 | A * | 5/1998 | Harman et al. | 600/459 |
| 6,425,865 | B1 * | 7/2002 | Salcudean et al. | 600/437 |
| 6,853,856 | B2 * | 2/2005 | Yanof et al. | 600/429 |
| 2002/0095139 | A1 * | 7/2002 | Keogh et al. | 600/235 |
| 2005/0059891 | A1 * | 3/2005 | Kosaku | 600/459 |
| 2009/0306515 | A1 * | 12/2009 | Matsumura et al. | 600/459 |
| 2012/0143172 | A1 * | 6/2012 | Oko et al. | 606/1 |

OTHER PUBLICATIONS

Cutkosky. "On grasp choice, grasp models, and the design of hands for manufacturing tasks". IEEE Transactiongs on Robotics and Automation. vol. 5, No. 3, pp. 269-279. IEEE, Jun. 1989.*

Boctor, et al., Robotically Assisted Intraoperative Ultrasound with Application to Ablative Therapy of Liver Cancer, Visualization, Image-Guided Procedures and Display, Proceedings of SPIE, 2003, pp. 281-291, vol. 5029.
Boctor, et al., A Dual-Armed Robotic System for Intraoperative Ultrasound Guided Hepatic Ablative Therapy: A Prospective Study, Proceedings for the 2004 IEEE International Conference on Robotics & Automation, 2004, 6 sheets.
Anonymous, et al., DaVinci Canvas: A Telerobotic Surgical System with Integrated, Robot-Assisted, Laparoscopic Ultrasound Capability, Med Image Comput Comput Assist Interv, 2005, 8 sheets, vol. 8, Pt 1, The Johns Hopkins University.
Budde, et al., Robot-Assisted Epicardial Ultrasound for Coronary Artery Localization and Anastomosis Quality Assessment in Totally Enoscopic Coronary Bypass Surgery, Medical Robotics, Jan. 2008, pp. 21-28, I-Tech Education and Publishing, Vienna, Austria.

* cited by examiner

*Primary Examiner* — Long V. Le
*Assistant Examiner* — Colin T Sakamoto
(74) *Attorney, Agent, or Firm* — Driggs, Hogg, Daugherty & Del Zoppo, Co. LPA

(57) ABSTRACT

An imaging probe includes a first nub protruding from an elongate housing in a direction away from the long axis and configured to be grasped by a robot apparatus performing a procedure of the object or subject to position the imaging probe in connection with a region of interest of the subject or object to image the region of interest with the probe. The imaging probe further includes at least one other nub located on and protruding from the elongate housing in a direction away from the long axis and configured to be grasped by a robot apparatus performing the procedure to facilitate grasping the first nub by the robot apparatus.

29 Claims, 4 Drawing Sheets

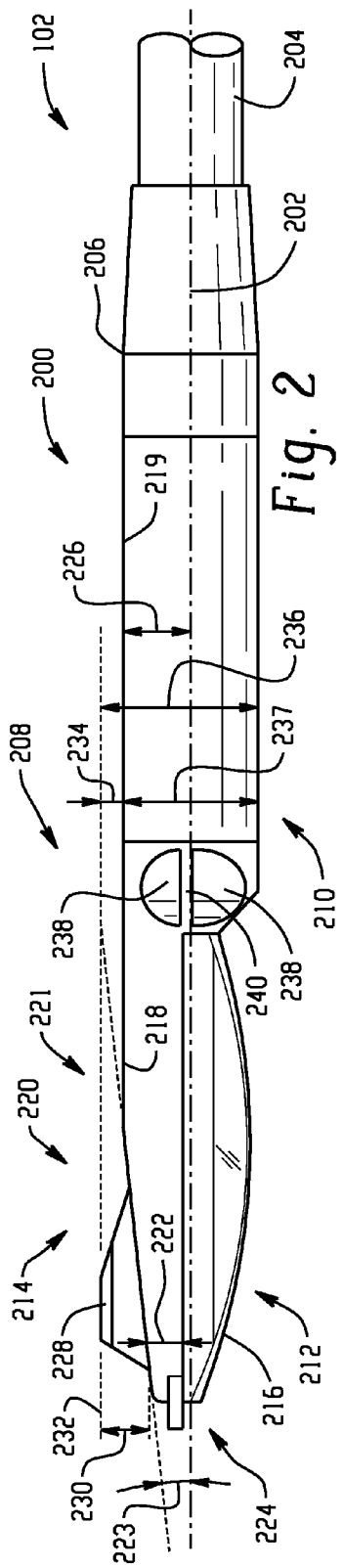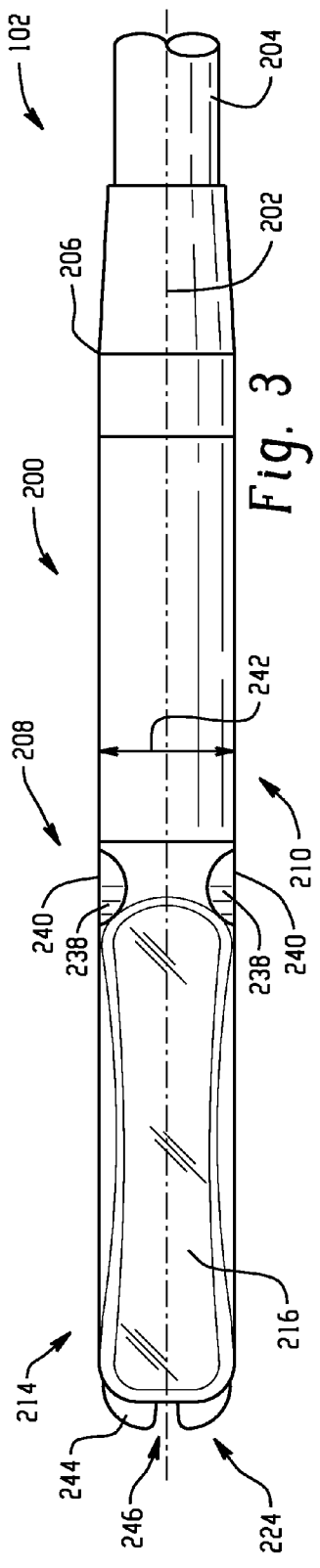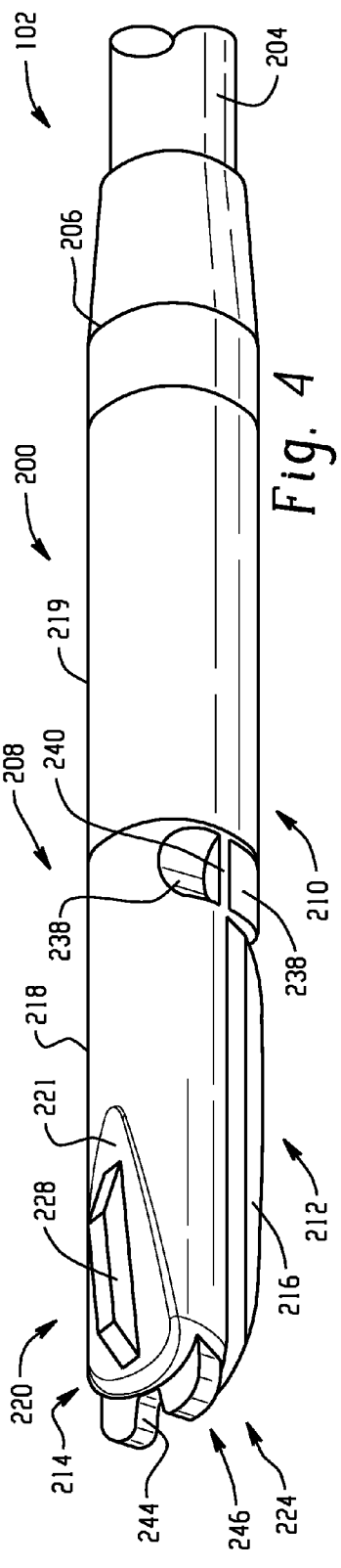

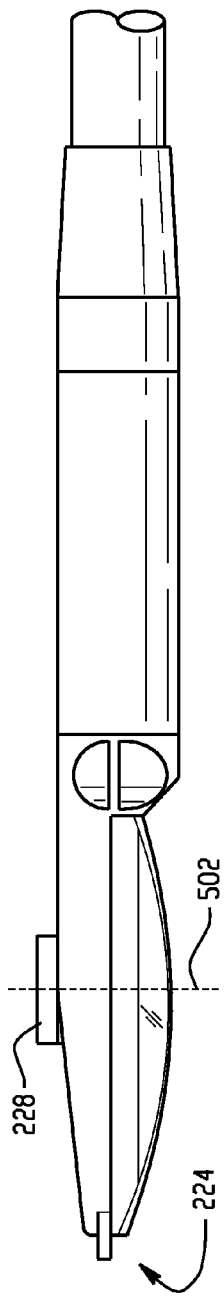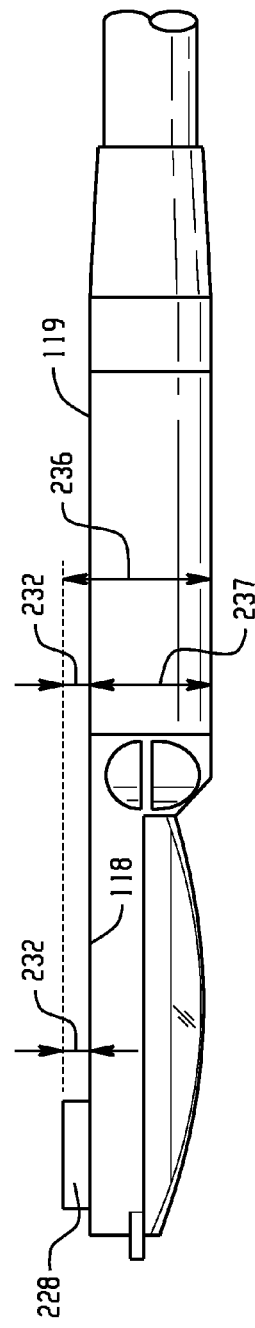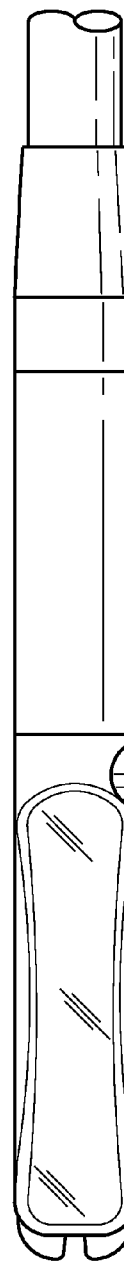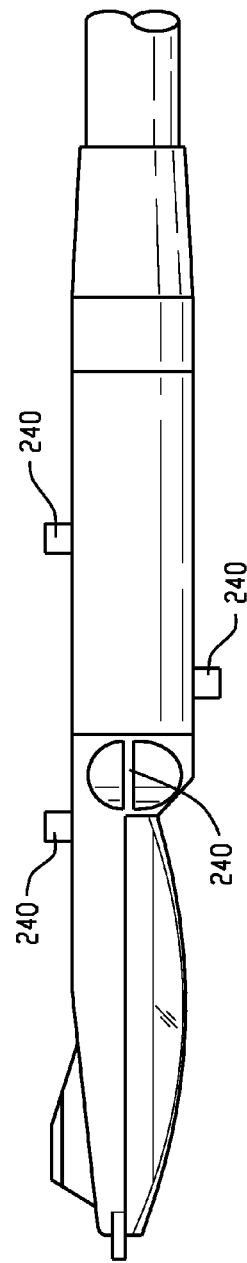

IMAGING PROBE

TECHNICAL FIELD

The following generally relates to an imaging probe that can be used in connection with robot assisted procedures, and more specifically to an imaging probe with nubs configured to be grasped by a robot for facilitating the robot assisted procedure, and is described with particular application herein to ultrasound (US) imaging.

BACKGROUND

Ultrasound imaging has provided useful information about the interior characteristics of an object or subject under examination. One application where ultrasound imaging may provide such useful information is with robot-assisted surgery. With robot-assisted surgery, one or more physicians remotely control a robot to perform surgery from a computer workstation, which may be located in the surgical room, outside of the surgical room and within the facility, or at a remote location. Signals from one or more cameras are fed back to the computer workstation and displayed to provide the one or more physicians with a virtual surgical site.

Generally, the robot has one or more arms with one or more graspers that can be moved through several degrees of freedom. The one or more physicians use the computer workstation to control, via hand and/or foot controls, the arms and graspers of the robot apparatus to pick up, employ, and set down various instruments such as cameras, scalpels, lights, tweezers, etc. for performing a surgical procedure. For minimally invasive surgery, the one or more physicians use the computer workstation to control the arms and graspers of the robot apparatus to move the various instruments through openings in devices such as trocars, cannulas, or the like, or other openings into the patient.

While performing a robot-assisted surgery, a physician may decide to image a region of interest, for example, in order to acquire images that reveal certain underlying anatomical structure such as vessels, organs, etc. Unfortunately, ultrasound imaging probes, structurally, have not been configured or are not well-suited to be grasped and held by a robot, moved through an opening in a trocar, cannula, etc. into a patient via a robot, and positioned with the robot therein with respect to a region of interest to image the region of interest. Thus, there is an unresolved need for other imaging probes.

SUMMARY

Aspects of the application address the above matters, and others.

In one aspect, an imaging probe includes an elongate housing with a first end region including a transducer array for scanning a subject or object and a second end region including probe electronics. The elongate housing extends along a long axis of the probe. The imaging probe further includes a first nub protruding from the elongate housing in a direction away from the long axis and configured to be grasped by a robot apparatus performing a procedure of the object or subject to position the imaging probe in connection with a region of interest of the subject or object to image the region of interest with the probe. The imaging probe further includes at least one other nub located on and protruding from the elongate housing in a direction away from the long axis and configured to be grasped by a robot apparatus performing the procedure to facilitate grasping the first nub by the robot apparatus. The imaging probe further includes an electrical interface configured to interface the probe electronics to an imaging console.

In another aspect, an imaging probe includes an elongate housing with a first end region including a transducer array for scanning a subject or object and a second end region including probe electronics. The elongate housing extends along a long axis of the probe. The imaging probe further includes a first nub protruding from the first end region in a direction away from the long axis and configured to be grasped by a robot apparatus performing a procedure of the object or subject to position the imaging probe in connection with a region of interest of the subject or object to image the region of interest with the probe.

In another aspect, a method includes grasping, with a robot apparatus, at least one nub protruding from an imaging probe, grasping, with the robot apparatus, a second nub protruding from the imaging probe after grasping the at least one nub with the robot apparatus, releasing the grasping of the at least one nub after grasping the second nub, and using the second nub to position the imaging probe in connection with a region of interest to scan the region of interest with the probe Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 2 schematically illustrates a side view of an example of the imaging probe of FIG. 1.

FIG. 3 schematically illustrates a top or bottom view of the example of the imaging probe of FIG. 2.

FIG. 4 schematically illustrates a perspective view of the example of the imaging probe of FIGS. 2 and 3.

FIG. 5 schematically illustrates a variation of the location of the primary nub of the imaging probe.

FIG. 6 schematically illustrates a variation of the tapering section of the imaging probe.

FIGS. 7 and 8 schematically illustrate a variation of the number and/or location of the secondary nubs of the imaging probe.

DETAILED DESCRIPTION

Figure 1:
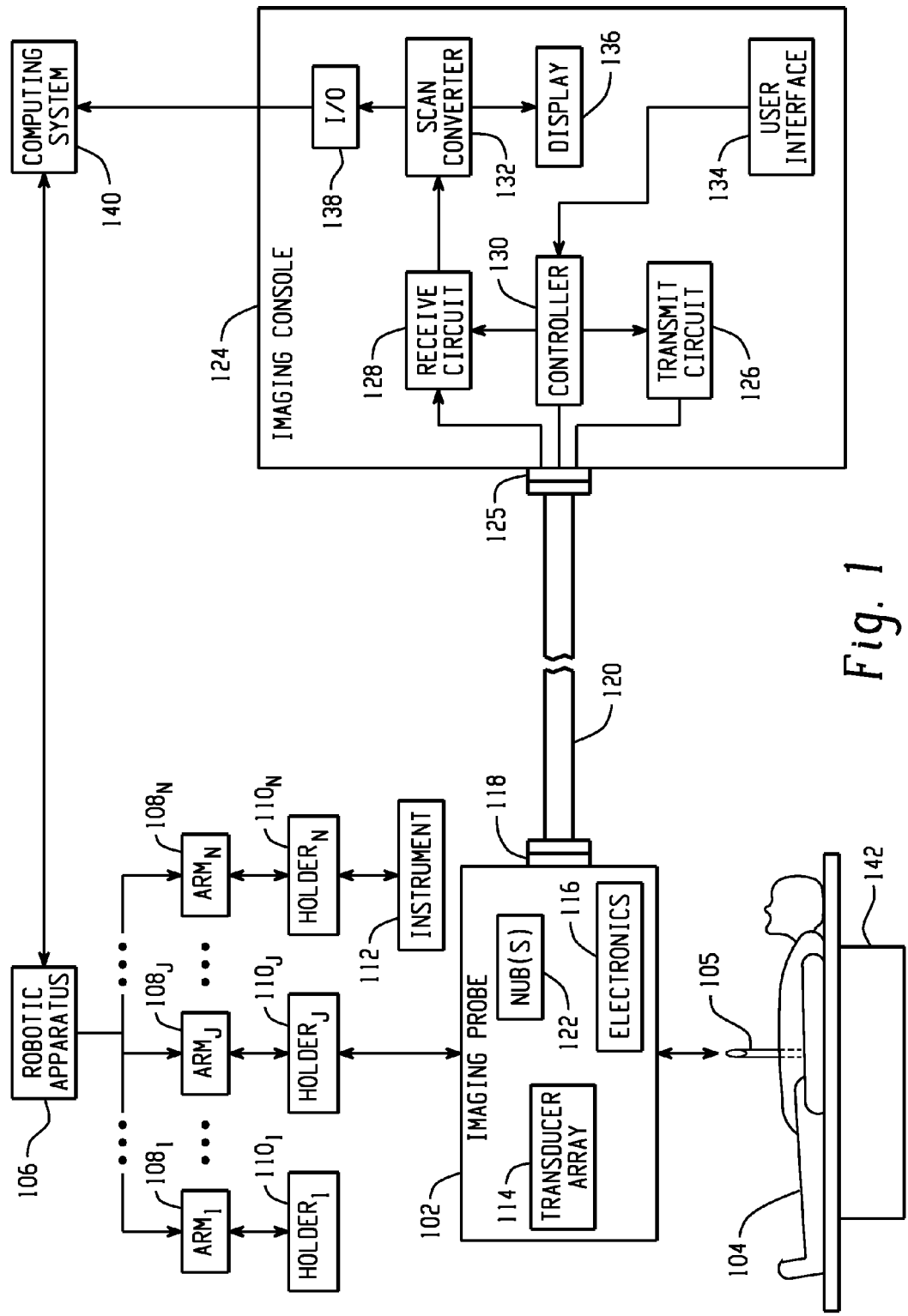
FIG. 1 schematically illustrates an exemplary imaging probe, such as an ultrasound imaging probe, in connection with various apparatuses used for a medical procedure of a subject.

FIG. 1 illustrates an exemplary imaging probe 102, such as an ultrasound transducer imaging probe, in connection with various apparatuses used for a medical procedure of a subject 104. However, it is to be understood that the procedure can be a non-medical procedure and/or the procedure can be performed on an object rather than the subject 104.

In the illustrated embodiment, one such apparatus includes a robot apparatus 106 such as a robotic medical procedure apparatus, which has been used in connection with laparoscopic, minimally invasive, and/or other medial procedures. As shown, the robot apparatus 106 includes N articulating arms 108 ($arm_1$ $108_1$, ..., $arm_J$ $108_J$, ..., and $arm_N$ $108_N$) respectively with N holders 110 ($holder_1$ $110_1$, ..., $holder_J$ $110_J$, ..., and $holder_N$ $110_N$) where J and N are integers equal to or greater than one, and N is equal to or greater than J. At least one of the holders 110 (e.g., the holders 110$_J$ and 110$_N$ in this example) is configured to grasp and hold one or more instruments such as a scalpel, a laser, tweezers, a camera or video recorder, a light, the imaging probe 102 (the holders 110$_J$), an instrument 112 (the holders 110$_N$), and/or other instrument.

At least one of the holders 110 includes movable (finger like) members arrange with respect to each other and configured to move in coordination with each other to behave similar to a human hand in that the members can move towards and away from each other to grasp and release an instrument. Additionally or alternatively, another of the holders 110 includes structure so that an instrument can be affixed to the holder 110. By way of example, the holder 110 may includes a threaded socket or a threaded protrusion configured to engage a complementary threaded protrusion or threaded socket of an instrument. Additionally or alternatively, another device such as a clamp, a magnet, etc. can be used to hold an instrument to the holders 110. Other mechanisms are also contemplated herein.

The illustrated imaging probe 102 includes a transducer array 114 with a one or two dimensional array of transducer elements, including linear, curved, circular, and/or other shaped arrays. The elements of the array can be concurrently and/or individually activated to transmit ultrasound signals and/or receive echo signals. The illustrated imaging probe 102 also includes electronics 116, which include electronics that route electrical signals within the imaging probe 102, for example, to and from the transducer array 114, and/or between the imaging probe 102 and a device external to the imaging probe 102 via an interface 118 and a pathway 120 such as a cable or the like electrically coupling the imaging probe 102 and the device.

The illustrated imaging probe 102 further includes an emitter 121 that emits a signal indicative of a spatial orientation of the emitter 121 and hence a spatial orientation of the probe 102. By way of example, in one non-limiting instance the emitter 121 includes one or more sensor coils, which, when subjected to a controlled, varying magnetic field, are induced by the field to produce a voltage. The induced voltage can be sensed by an electromagnetic spatial measurement system or other system and used provide spatial orientation information of the emitter 121. In one instance, the varying magnetic field has a low field strength and can safely pass through human tissue. As such, the one or more sensor coils can be induced to produce a voltage which can be sensed to determine spatial location without a line-of-sight constraint such as that of an optical spatial measurement system. An example of such a suitable spatial measurement system is the Aurora® System, which is a product of NDI, a company headquartered in Ontario, Canada, and example of suitable sensor coils include the Aurora 5DOF sensors and/or the Aurora 6DOF sensors. An optical or other spatial measurement system can additionally or alternatively be employed. In another embodiment, the emitter 121 is omitted.

The illustrated imaging probe 102 also includes one or more protruding structures or nubs 122 configured to be grasped by at least one of the holders 110 of one of the arms 108 of the robot apparatus 106. As described in greater detail below, at least one of the nubs 122, for example, a primary one of the nubs 122, is configured for moving and/or positioning the imaging probe 102 during a medical procedure (including into and out of a cavity of the patient 104 via an opening into the cavity such as through a device 105 like a trocar, cannula, etc.), and one or more other nubs 122, for example, one or more secondary nubs 122, are used to facilitate grasping the primary nub 122 with the holder 110. It is to be appreciated that using the one or more secondary nubs 122 as such may improve ease of suitably grasping the primary nub 122, relative to a configuration in which the imaging probe 102 does not include any secondary nubs 122. As an analogy, in some instances it is easier for a person to suitably grasp an instrument using both of their hands rather than just one of their hands.

Also described in greater detail below, in one instance the primary nub 122 is arranged with respect to the imaging probe 102 such that a largest geometric dimension of the imaging probe 102, with the primary nub 122, entering the device 105 is about a same size or only slightly larger than a corresponding geometric dimension of the imaging probe 102 without the nub 122. This may allow for minimizing an increase in size of the entry passageway in to the subject and the diameter of device 105 to accommodate the primary nub 122, relative to a configuration in which the primary nub 122 further increases the geometric dimension of the imaging probe 102 entering the device 105. Furthermore, with such a configuration, the pivot point for maneuvering the imaging probe 102 will be located nearer to the tip of the probe 102. As a result, the extent of the probe 102 entering the patient 104 may be reduced and/or the accuracy of positioning of the probe 102 in the patient 104 may be improved, relative to a configuration in which the primary nub 122 is located farther away from the tip.

Another of the various other apparatuses shown in FIG. 1 is an imaging console 124 such as an ultrasound imaging console. In the illustrated embodiment, the ultrasound imaging console 124 is in electrical communication with the imaging probe 102. More particularly, the ultrasound imaging console 124 includes an interface 125 configured to mechanically and electrically couple with the pathway 120 and hence the imaging probe 102. The connection between the interface 125 and the pathway is releasable and can be released to disconnect the imaging probe 102 from the ultrasound imaging console 124 and/or install a different imaging probe for use with the ultrasound imaging console 124.

The illustrated ultrasound imaging console 124 includes a transmit circuit 126 that controls phasing and/or time of actuation of the elements of the transducer array 114, which allows for steering and/or focusing the transmitted beam from predetermined origins along the array and at predetermined angles. The ultrasound imaging console 124 also includes receive circuit 128 that receives the echoes received by the transducer array 114. For B-mode and/or other applications, the receive circuit 128 beamforms (e.g., delays and sums) the echoes from the transducer elements into a sequence of focused, coherent echo samples along focused scanlines of a scanplane. The receive circuit 128 may additionally or alternatively be configured for other ultrasound imaging and/or processing modes.

A controller 130 of the ultrasound imaging console 124 controls the transmit circuit 126 and/or the receive circuit 128. Such control may include, but is not limited to, controlling the frame rate, number of scanline groups, transmit angles, transmit energies, transmit frequencies, transmit and/or receive delays, the imaging mode (e.g., B-mode, C-mode, Doppler, etc.), etc. A scan converter 132 of the ultrasound imaging console 124 scan converts the frames of data to generate data for display, for example, by converting the data to the coordinate system of the display. The scan converter 132 can be configured to employ analog and/or digital scan converting techniques.

A user interface 134 includes various input and/or output devices for interacting with the controller 130, for example, to select a data acquisition mode, a data processing mode, a data presentation mode, etc. The user interface 134 may include various controls such as buttons, knobs, a keypad, a touch screen, etc. The user interface 134 may also include various types of visual and/or audible indicators. A display 136 can be used to present the acquired and/or processed data. Such presentation can be in an interactive graphical user interface (GUI), which allows the user to selectively rotate, scale, and/or manipulate the displayed data. Such interaction can be through a mouse or the like and/or a keyboard or the like. Input/output (I/O) 138 provides for communication of information between the imaging console 124 and other apparatuses.

A computing system 140 serves as an operator console for the robot apparatus 106. The computing system 140 includes a display(s), a processor(s) and physical memory encoded with computer executable instructions, which, when executed by the one or more processors, cause the computing system 140 to carry out various functions. This includes running a software application that allows a user of the computing system 140 to control the robot apparatus 106, for example, to move one or more of the arms 108, grasp or release an instrument via one or more of the graspers 110, maneuver a grasped instrument, etc. In one non-limiting instance, this includes sensing the user's hand movements, generating an electrical signal indicative thereof, and conveying the signal to a controller of the robot apparatus 106. Controls of the system 140 may include hand and/or foot based controls. The one or more displays are used to visually present information from the robot apparatus and/or the imaging console 124.

In the illustrated embodiment, the robot apparatus 106 is used to facilitate performing a medical procedure on the subject 104 supported by a subject support 142. For the medical procedure, the user of the computing system 140 controls the robot apparatus 106 via the computing system 140 to position the imaging probe 102 in a cavity of the subject such as the abdomen via the device 105, which, as noted herein, can be a trocar, cannula or the like for scanning within the subject 104. The robot apparatus 106 can retrieve the imaging probe 102 from a table side tray or cart, receive it from the user or other personnel, grasp it once the user or authorized personnel places it in the device 105, and/or otherwise receive it. The robot apparatus 106 can also remove the imaging probe 102 and place it back on the table, deliver it to personnel, etc. One or more other openings into the subject can be used to guide one or more other instruments into the cavity of the subject 104.

FIGS. 2, 3, and 4 respectively illustrate a side view, a top or bottom view, and a perspective view of an example of the imaging probe 102.

As shown, in this example the imaging probe 102 includes an elongate housing portion 200 extending along a longitudinal axis 202 of the imaging probe 102, an electrical conductor pathway such as a flexible cable 204, and a strain or flex relief portion 206 coupling the housing portion 200 and the flexible cable 204.

The housing portion 200 includes include a first end region 208 and a second end region 210, which is coupled to the flex relief portion 206. The first end region 208 includes an imaging side 212 and an opposing side 214, which opposes the imaging side 212 with respect to the axis 202 and faces the other way. The imaging side 212 includes an acoustic window 216, with the transducer array 114 (not visible) disposed behind the acoustic window 216, which facilitates transmission and reception of acoustic signal and echoes from and to the transducer array 114. The second end region 210 houses a majority of the electronics 116 of the imaging probe 102. Generally, the geometry or volume of the second end region 210 is limited by the space needed to house the electronics 116.

The opposing side 214 of the first end region 208 includes a major surface 218 that is contiguous with a major surface 219 of the second end region 210. In the illustrated embodiment, a sub-portion 221 of the major surface 218 of the opposing side 214 has a tapering section 220, which tapers towards the axis 202 such that a depth 222 of the sub-portion 221 from the surface 218 to the axis 202 nearer to a tip 224 of the probe 102 is less than a depth 226 from the major surface 219 of the second end region 210 to the axis 202. The tapering section 220 tapers at a predetermined angle 223 with respect to the long axis 202 of the probe 102.

A primary nub 228 of the nubs 122 (FIG. 1) is located on the tapering section 220 adjacent to the tip 224. As such, a pivot point of the robot apparatus 106 for maneuvering the transducer array 114 in the cavity of the subject 104 is close to the tip, which may increase a positional resolution at which the transducer array 114 can be maneuvered when in the cavity of the subject 104. Moving the primary nub 228 towards or into the second end region 210 will move the pivot point away from the tip 224, which may reduce the positional resolution at which the transducer array 114 can be maneuvered when in the cavity of the subject 104. In the illustrated embodiment, the primary nub 228 is part of the sub-portion 221. In another instance, the primary nub 228 may be a separate component either permanently or removeably affixed to the sub-portion 221.

As shown in FIG. 2, the primary nub 228 has a peak height 232. In the illustrated embodiment, due to the tapering section 220, a distance 230 from the surface 218 of the first region 208 to the peak height 232 of the primary nub 228 is greater than a distance 234 from the surface 219 of the second region 210 to the peak height 232. A maximum depth 236 of the imaging probe 102 includes a summation of a depth 237 of the second end region and the depth 234. Moving the primary nub 228, for the given peak height 232, more towards or into the second end region 210 will increase the maximum depth 236 of the probe 102, potentially requiring a larger diameter device 105 (FIG. 1) for inserting the imaging probe 102 into the cavity of the subject 104.

In the illustrated embodiment, at least two secondary nubs 240 of the nubs 122 (FIG. 1) are also located the first end region 208. In this example, the nubs 240 are located in recesses 238 of the first end region 208. The geometry of the recesses 238 and the at least two secondary nubs 240 is such that the at least two secondary nubs 240 do not increase a maximum width 242 (FIG. 3) of the probe 102. In one instance, the nubs 240 extend to the width 242, while in another instance the nubs 240 do not extend as far as the width 242. In the illustrated embodiment, the secondary nub 240 is part of the first end region 208. In another instance, the secondary nub 240 may be a separate component either permanently or removeably affixed to the probe 102.

The illustrated imaging probe 102 also includes a protrusion 244 (FIGS. 3 and 4) extending from the tip 224 along the axis 202. The protrusion 244 includes a recess 246 configured to support a biopsy needle and/or other instrument. The protrusion 244 may also be used to identify the scan plane. The protrusion is not number in FIG. 2 due to limited space.

In one non-limiting embodiment, a length of the housing 200 is a value in a range from about ten (10) to ninety (90) millimeters such as twenty (20) millimeters, seventy-four (74) millimeters, etc., a length of the first end region 208 is a value in a range from about fifteen (15) to fifty-five (55) millimeters such as forty (40) millimeters, and a maximum depth of the first end region 208 with nub 228 is a value in a range from about eight (8) to thirteen (13) millimeters such as ten and seven tenths (10.7) millimeters.

Variations are contemplated.

In the illustrated embodiment, the primary nub 228 is located proximate to the tip 224 of the imaging probe 102. In another instance, the primary nub 228 is located farther away from the tip 224 of the imaging probe 102. One example of this instance is shown in FIG. 5, in which the primary nub 228 is located at approximately a center region 502 of the transducer array 114 (not visible). Other locations between those shown in FIGS. 2-5 and outside thereof are also contemplated herein.

In the illustrated embodiment, the first end region 208 includes the tapering section 220. In another instance, the section 220 does not taper but instead extends parallel with the axis 202, for example, along with the remaining portion of surface 218 and the surface 219. An example of this instance is shown in FIG. 6. In this instance, the distance 236 will be larger than that in FIGS. 2-4 and will be approximately equal the summation of the distance 237 and the peak height 232.

The illustrated embodiment includes two secondary nubs 240. In another instance, the probe 102 includes a single secondary protruding structure 240 (as shown in FIG. 7) or more than two secondary protruding structures 240 (as shown in FIG. 8) in similar or different locations (also shown in FIG. 8).

In the illustrated embodiment, the at least one secondary nub 240 protrudes so that it does not increase the width 242 of the probe 102 relative to a configuration in which the at least one secondary protruding structure 240 is omitted. In yet another instance, the at least one secondary nub 240 protrudes and increases the maximum width 242 of the probe 102.

It is to be appreciated that the illustrated size and/or shape of the nubs 228 and/or 240 is for explanatory purposes and other sizes and/or shapes are contemplated herein.

Figure 9:
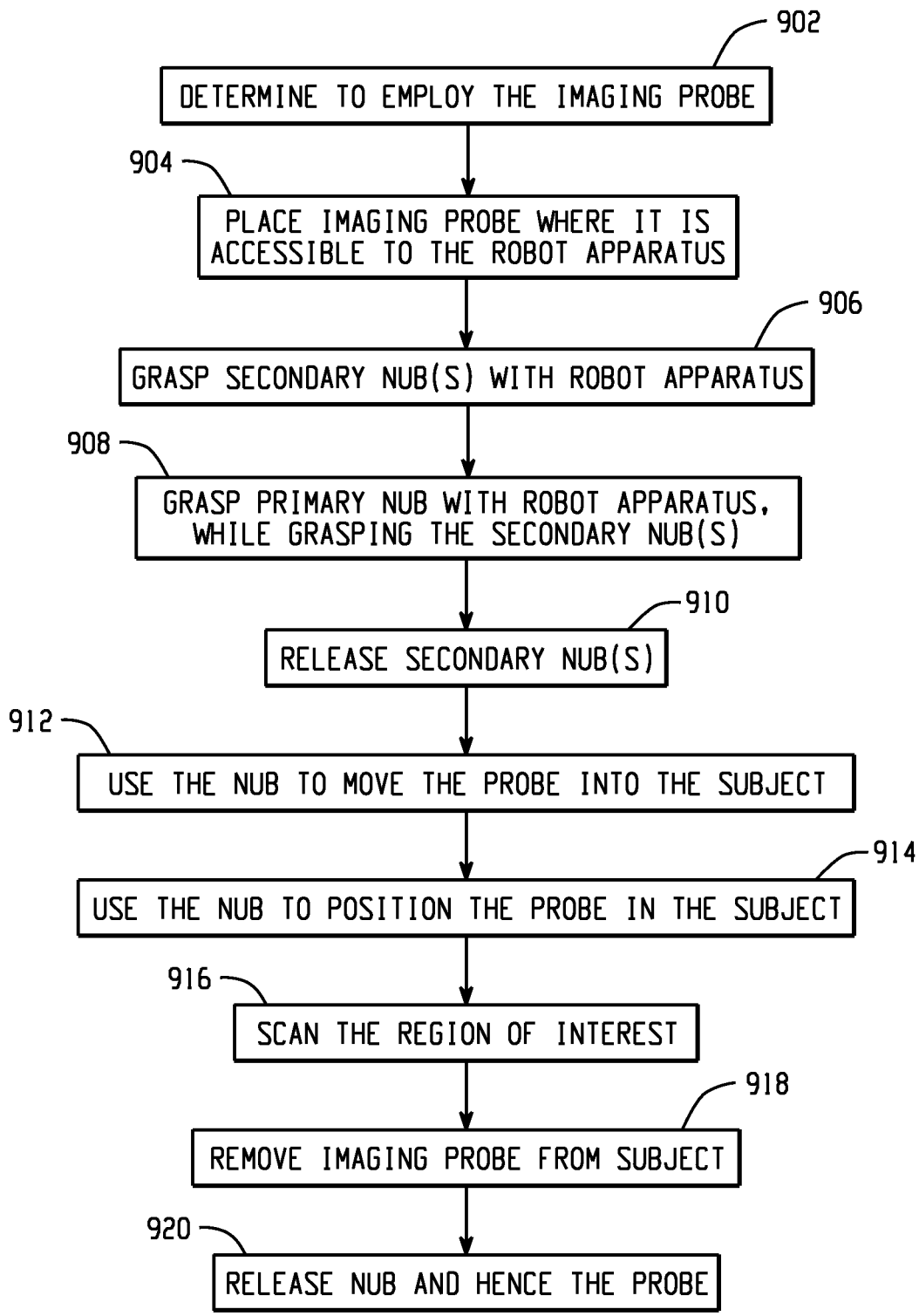
FIG. 9 illustrates an example method in accordance with the exemplary imaging probe.

FIG. 9 illustrates a method for using the imaging probe 102. For explanatory purposes, the method is described in the context of performing a procedure within a cavity of the subject 104 through the device 105.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 902, the person(s) controlling the robot apparatus 106 to perform the procedure determines to employ the imaging probe 102 to image structure from within the cavity of the subject 104.

At 904, if not already in a location where the robot apparatus 106 can retrieve the imaging probe 102, the imaging probe 102 is moved to such a location. For example, personnel can place the imaging probe 102 on a cart accessible to the robot apparatus 106, in the device 105, and/or at another location where it is retrievable by the robot apparatus 106.

At 906, the robot apparatus 106 is controlled to grasp and hold at least one of the secondary nubs 240 with a holder 100 of an arm 108 of the robot apparatus 106.

At 908, while the robot apparatus 106 grasps and holds the least one of the secondary nubs 240, the robot apparatus 106 is controlled to grasp and hold the primary nub 228 with another holder 110 of another arm 108 of the robot apparatus 106.

At 910, the robot apparatus 106 is controlled to release the at least one of the secondary nubs 240 with the holder 110 of the arm 108.

At 912, the robot apparatus 106 is controlled to move, via the primary nub 228, at least a portion of the imaging probe 102 with the transducer array 114 into the cavity of the subject 104 through the opening provided by the device 105.

At 914, the robot apparatus 106 is controlled to move the imaging probe 102 via the primary nub 228 within the cavity of the subject 104 to position the imaging probe 102 to scan a region of interest.

At 916, the imaging probe 102 is activated to scan the region of interest.

At 918, the robot apparatus 106 is controlled to remove the portion of the imaging probe 102 in the cavity from the cavity via the opening provided by the device 105.

At 920, the robot apparatus 106 is controlled to release the primary nub 228 and hence the imaging probe 102. The probe 102 can be released and set back onto the cart, in the hand of personnel, etc.

Although the above is described in the context of using the imaging probe 102 inside the subject 104, it is to be understood that the robot apparatus 106 can similarly use the imaging probe 102 for procedures outside of the subject 104.

It is to be appreciated that the methods herein may be implemented by one or more processors executing computer executable instructions stored, encoded, embodied, etc. on computer readable storage medium such as computer memory, non-transitory storage, etc. In another instance, the computer executable instructions are additionally or alternatively stored in transitory or signal medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An imaging probe, comprising:
   an elongate housing, extending along a longitudinal axis, the elongate housing, including:
   a first end region, including:
   a tip;
   an imaging side, including:
   a transducer array; and
   an opposing side, which opposes the imaging side, with respect to the longitudinal axis and faces away from the imaging side, the opposing side, including:
   a major surface, wherein a sub-portion of the major surface tapers towards the longitudinal axis in a direction of the tip; and
   a first nub, disposed adjacent to the tip, protruding from the sub-portion of the major surface in a direction away from the longitudinal axis and the imaging side.

2. The imaging probe of claim 1, wherein a first distance from the sub-portion of the major surface to a peak height of the first nub is greater nearer the tip than a second distance from the sub-portion of the major surface to the peak height of the first nub further away from the tip.

3. The imaging probe of claim 1, wherein the first nub is located in a region approximately inline with a center region of the transducer array.

4. The imaging probe of claim 1, wherein the first nub is located between the tip of the probe and a region approximately inline with a center region of the transducer array.

5. The imaging probe of claim 2, wherein the first distance, is less than a distance between the major surface and the longitudinal axis.

6. The imaging probe of claim 1, wherein a maximum depth of the first end region with the first nub nearer the tip is less than a depth of the first end region further away from the tip.

7. The imaging probe of claim 1, further comprising:
at least one other nub disposed on and protruding from the elongate housing in a direction away from the long axis, the first nub and the transducer array, wherein the first end region has a width, and at least one recess is located along the width, and the at least one other nub extends in the recess.

8. The imaging probe of claim 7, wherein the at least one other nub does not extend outside of the recess.

9. The imaging probe of claim 1, further comprising:
a protrusion protruding from the tip of the probe and extending from the tip along the longitudinal axis.

10. The imaging probe of claim 9, wherein the protrusion includes a recess configured to support an instrument.

11. The imaging probe of claim 1, wherein the first nub is not a needle guide.

12. The imaging probe of claim 11, further comprising:
a protrusion protruding from the tip of the probe and extending from the tip along the longitudinal axis, wherein the protrusion is a needle.

13. The imaging probe of claim 1, further comprising:
an electrical interface configured to interface probe electronics to an imaging console, wherein the electrical interface is in physical and electrical communication with a complementary interface of an ultrasound imaging console.

14. The imaging probe of claim 1, wherein the imaging probe is an ultrasound imaging probe.

15. An imaging probe, comprising:
an elongate housing, extending along a longitudinal axis, the elongate housing, including:
a first end region, including:
a tip;
an imaging side, including:
a transducer array disposed along the longitudinal axis; and
an opposing side, which opposes the imaging side; and
a first nub, disposed adjacent to the tip, protruding from a tapered region of the opposing side in a direction away from the long axis, opposite the direction of the imaging side,
wherein a first distance from the tapered region a peak height of the first nub is greater nearer the tip than a second distance from the tapered region to the peak height of the first nub further away from the tip, wherein the peak height is relative to the tapered region.

16. The imaging probe of claim 15, wherein the sub-portion tapers such that a depth of the first end region is smaller nearer the tip and greater further away from the tip.

17. The imaging probe of claim 15, wherein the first nub is located between the tip of the probe and a region approximately inline with a center region of the transducer array.

18. The imaging probe of claim 15, the elongate housing, further comprising:
a second end region, wherein a maximum depth of the first end region with the first nub is less than a depth of a sum of a maximum depth of the second end region and a maximum length from the tapered region to the peak height of the nub.

19. The imaging probe of claim 15, further comprising:
at least one other nub protruding from the elongate housing in a direction away from the longitudinal axis, the first nub and the imaging side.

20. The imaging probe of claim 19, wherein the first end region includes at least one recess, and the at least one other nub is located in the recess.

21. The imaging probe of claim 20, wherein the at least one other nub does not extend out of the recess.

22. The imaging probe of claim 15, further comprising:
a protrusion at a tip of the probe.

23. The imaging probe of claim 22, wherein the protrusion at least one of supports an instrument or identifies a scan plane.

24. A method, comprising:
obtaining an imaging probe that includes at least one nub protruding from the imaging probe, an elongate housing, extending along a longitudinal axis, the elongate housing, including: a first end region, including: a tip; an imaging side, including: a transducer array; an opposing side, which opposes the imaging side, with respect to the longitudinal axis and faces away from the imaging side, the opposing side, including: a major surface, wherein a sub-portion of the major surface tapers towards the longitudinal axis in a direction of the tip; and a second end region is coupled to the first end region; and a second nub protruding from the imaging probe located adjacent to the tip and protrudes from the sub-portion of the major surface in a direction away from the longitudinal axis, opposite the direction of the imaging side;
grasping, with a robot apparatus, the at least one nub;
grasping, with the robot apparatus, the second nub after grasping the at least one nub with the robot apparatus;
releasing the grasping of the at least one nub after grasping the second nub; and
using the second nub to position the imaging probe in connection with a region of interest to scan the region of interest with the probe.

25. The method of claim 24, wherein the region of interest is internal to an object or subject, and further comprising:
moving the imaging probe, via the second nub and with the robot apparatus, through an opening in a device providing an entryway into the object or subject to move the imaging probe from outside of the object or subject into a cavity internal to the object or subject.

26. The method of claim 24, further comprising:
grasping, with the robot apparatus, a third nub protruding from the imaging probe after grasping the at least one nub with the robot apparatus, wherein the third nub is located on and protrudes from at least another recess of the first end region in a direction away from the longitudinal axis, the opposing side and the imaging side, wherein the at least another recess is located on a side opposing the at least one recess.

27. The method of claim 26, further comprising:
grasping, with the robot apparatus, a fourth nub protruding from the imaging probe after grasping the at least one nub with the robot apparatus, wherein the fourth nub is located on the imaging side or the opposing side.

28. The method of claim 24, wherein the second nub is located between a tip of the imaging probe and a region approximately inline with a center region of the transducer array.

29. The method of claim 24, wherein the at least one nub is disposed on and protrudes from at least one recess of the first end region in a direction away from the longitudinal axis, the opposing side and the imaging side, and wherein the at least one nub does not extend out passed the recess.

* * * * *